(12) United States Patent
Weinstock

(10) Patent No.: US 12,226,345 B2
(45) Date of Patent: Feb. 18, 2025

(54) NEAR EYE REFLECTIVE DEVICES FOR DIAGNOSTIC AND THERAPEUTIC OPHTHALMIC PROCEDURES

(71) Applicant: ViaLase, Inc., Aliso Viejo, CA (US)

(72) Inventor: Robert Weinstock, Largo, FL (US)

(73) Assignee: ViaLase, Inc., Aliso Viejo, CA (US)

( * ) Notice: Subject to any disclaimer, the term of this patent is extended or adjusted under 35 U.S.C. 154(b) by 544 days.

(21) Appl. No.: 17/121,636

(22) Filed: Dec. 14, 2020

(65) Prior Publication Data

US 2021/0307962 A1   Oct. 7, 2021

Related U.S. Application Data

(60) Provisional application No. 62/948,227, filed on Dec. 14, 2019.

(51) Int. Cl.
| | | |
|---|---|---|
| A61F 9/008 | (2006.01) | |
| A61F 9/007 | (2006.01) | |
| A61F 9/009 | (2006.01) | |

(52) U.S. Cl.
CPC .......... *A61F 9/008* (2013.01); *A61F 9/00781* (2013.01); *A61F 9/009* (2013.01); *A61F 9/00825* (2013.01); *A61F 2009/00851* (2013.01); *A61F 2009/00868* (2013.01); *A61F 2009/00891* (2013.01); *A61F 2009/00897* (2013.01)

(58) Field of Classification Search
CPC ...... A61F 9/008; A61F 9/00781; A61F 9/009; A61F 2009/00851; A61F 2009/00868; A61F 2009/00891; A61F 2009/00897
See application file for complete search history.

(56) References Cited

U.S. PATENT DOCUMENTS

| | | | | |
|---|---|---|---|---|
| 4,423,931 A | * | 1/1984 | Shapiro | A61B 3/1225 356/604 |
| 5,123,902 A | * | 6/1992 | Muller | A61B 18/20 606/4 |
| 5,549,596 A | | 8/1996 | Latina | |
| 6,004,314 A | | 12/1999 | Wei et al. | |
| 6,033,396 A | | 3/2000 | Huang et al. | |
| 6,059,772 A | | 5/2000 | Hsia et al. | |
| 6,251,103 B1 | | 6/2001 | Berlin | |

(Continued)

FOREIGN PATENT DOCUMENTS

| | | |
|---|---|---|
| CN | 104382689 B | 9/2016 |
| CN | 113662507 A | 11/2021 |

(Continued)

OTHER PUBLICATIONS

International Search Report, International Patent Application No. PCT/US2020/064947, Apr. 20, 2021, 3 pgs.

(Continued)

*Primary Examiner* — Lynsey C Eiseman
*Assistant Examiner* — Skylar Lindsey Christianson
(74) *Attorney, Agent, or Firm* — LOZA & LOZA, LLP; David S. Sarisky

(57) ABSTRACT

Systems and methods for performing laser operations on the structures of the eye, including the drain angle, trabecular mesh and the area of the eye where the iris and cornea meet. Laser systems and methods for treating glaucoma. Laser assisted MIGS procedures.

11 Claims, 10 Drawing Sheets

(56) References Cited

U.S. PATENT DOCUMENTS

| | | |
|---|---|---|
| 6,482,199 B1 | 11/2002 | Neev |
| 6,682,523 B2 | 1/2004 | Shadduck |
| 6,989,007 B2 | 1/2006 | Shadduck |
| 7,131,968 B2 | 11/2006 | Bendett et al. |
| 7,192,412 B1 | 3/2007 | Zhou et al. |
| 7,282,046 B2 | 10/2007 | Simon |
| 7,351,241 B2 | 4/2008 | Bendett et al. |
| 7,771,417 B2 | 8/2010 | Telfair et al. |
| 8,011,504 B1 | 9/2011 | Farberov |
| 8,171,937 B2 | 5/2012 | Bendett et al. |
| 8,230,866 B2 | 7/2012 | Hauger et al. |
| 8,394,084 B2 | 3/2013 | Palankar et al. |
| 8,523,926 B2 | 9/2013 | Neev |
| 8,540,659 B2 | 9/2013 | Berlin |
| 8,568,393 B2 | 10/2013 | Palanker |
| 8,585,686 B2 | 11/2013 | Bergt et al. |
| 8,679,089 B2 | 3/2014 | Berlin |
| 8,687,866 B2 | 4/2014 | Marziliano et al. |
| 8,709,001 B2 | 4/2014 | Blumenkranz et al. |
| 8,747,395 B2 | 6/2014 | Rathjen |
| 8,845,624 B2 | 9/2014 | Raksi et al. |
| 8,920,407 B2 | 12/2014 | Raksi et al. |
| 9,028,069 B2 | 5/2015 | Rathjen |
| 9,033,963 B2 | 5/2015 | Vera et al. |
| 9,044,303 B2 | 6/2015 | Kurtz et al. |
| 9,101,448 B2 | 8/2015 | Blumenkranz et al. |
| 9,259,153 B2 | 2/2016 | Goto |
| 9,259,354 B2 | 2/2016 | Horvath et al. |
| 9,265,411 B2 | 2/2016 | Chen et al. |
| 9,271,870 B2 | 3/2016 | Palanker et al. |
| 9,301,878 B2 | 4/2016 | Raksi et al. |
| 9,320,650 B2 | 4/2016 | Bendett et al. |
| 9,441,946 B2 | 9/2016 | Massow et al. |
| 9,456,925 B2 | 10/2016 | Kurtz et al. |
| 9,474,648 B2 | 10/2016 | Palanker et al. |
| 9,498,295 B2 | 11/2016 | Palanker |
| 9,517,006 B2 | 12/2016 | Izatt et al. |
| 9,554,702 B2 | 1/2017 | Papac et al. |
| 9,560,963 B2 | 2/2017 | Buckland et al. |
| 9,603,741 B2 | 3/2017 | Berlin |
| 9,603,744 B2 | 3/2017 | Hailmann et al. |
| 9,629,750 B2 | 4/2017 | Dambacher et al. |
| 9,642,746 B2 | 5/2017 | Berlin |
| 9,681,985 B2 | 6/2017 | Andersen et al. |
| 9,724,238 B2 | 8/2017 | Heitel |
| 9,750,640 B2 | 9/2017 | Palanker et al. |
| 9,820,883 B2 | 11/2017 | Berlin |
| 9,833,357 B2 | 12/2017 | Berlin |
| 9,844,464 B2 | 12/2017 | Bendett et al. |
| 9,936,868 B2 | 4/2018 | Izatt et al. |
| 10,064,757 B2 | 9/2018 | Berlin |
| 10,073,515 B2 | 9/2018 | Awdeh |
| 10,159,600 B2 | 12/2018 | Horvath et al. |
| 10,159,601 B2 | 12/2018 | Berlin |
| 10,165,941 B2 | 1/2019 | Walsh et al. |
| 10,179,066 B2 | 1/2019 | Badawi et al. |
| 10,195,078 B2 | 2/2019 | Horvath et al. |
| 10,195,079 B2 | 2/2019 | Horvath et al. |
| 10,195,080 B2 | 2/2019 | Berlin |
| 10,238,281 B2 | 3/2019 | Isogai et al. |
| 10,238,541 B2 | 3/2019 | Yee et al. |
| 10,292,868 B2 | 5/2019 | Chew et al. |
| 10,335,314 B2 | 7/2019 | Berlin |
| 10,335,315 B2 | 7/2019 | Goldshleger et al. |
| 10,360,683 B2 | 7/2019 | Iwase et al. |
| 10,362,935 B2 | 7/2019 | Dastmalchi et al. |
| 10,362,936 B2 | 7/2019 | Buckland et al. |
| 10,363,169 B2 | 7/2019 | Belkin et al. |
| 10,363,172 B2 | 7/2019 | Kawai et al. |
| 10,383,689 B2 | 8/2019 | Berlin |
| 10,390,883 B2 | 8/2019 | Deladurantaye et al. |
| 10,398,306 B2 | 9/2019 | Liu |
| 10,406,034 B2 | 9/2019 | Siegele |
| 10,426,548 B2 | 10/2019 | Tearney et al. |
| 10,454,237 B2 | 10/2019 | Yu et al. |
| 10,456,030 B2 | 10/2019 | Buckland et al. |
| 10,456,209 B2 | 10/2019 | Peyman |
| 10,478,060 B2 | 11/2019 | Kubota |
| 10,493,274 B2 | 12/2019 | Irazoqui et al. |
| 10,499,809 B2 | 12/2019 | Kalina, Jr. et al. |
| 10,500,094 B2 | 12/2019 | Buzawa et al. |
| 10,517,760 B2 | 12/2019 | Berlin |
| 10,524,822 B2 | 1/2020 | Aljuri et al. |
| 10,537,476 B2 | 1/2020 | Ha et al. |
| 10,542,883 B2 | 1/2020 | Gooi et al. |
| 10,543,122 B2 | 1/2020 | Kahook |
| 10,543,123 B2 | 1/2020 | Neev |
| 10,568,763 B2 | 2/2020 | Vera et al. |
| 10,588,694 B1 | 3/2020 | Neev |
| 10,596,036 B2 | 3/2020 | Pinchuk |
| 10,603,214 B2 | 3/2020 | Bigler et al. |
| 10,603,216 B2 | 3/2020 | Kurtz et al. |
| 10,653,557 B2 | 5/2020 | Rill et al. |
| 10,674,906 B2 | 6/2020 | Kalina, Jr. et al. |
| 10,687,978 B2 | 6/2020 | Berlin |
| 10,702,416 B2 | 7/2020 | Belkin et al. |
| 10,744,033 B2 | 8/2020 | Baerveldt et al. |
| 10,744,034 B2 | 8/2020 | Homer |
| 10,758,418 B2 | 9/2020 | Vold et al. |
| 10,765,559 B2 | 9/2020 | Berlin |
| 10,779,988 B2 | 9/2020 | Fu et al. |
| 10,799,113 B2 | 10/2020 | Vadakke Matham et al. |
| 10,821,023 B2 | 11/2020 | Raksi |
| 10,821,024 B2 | 11/2020 | Raksi |
| 10,888,461 B2 | 1/2021 | Orthaber et al. |
| 10,898,381 B2 | 1/2021 | Bendett et al. |
| 11,019,996 B2 | 6/2021 | Kalina, Jr. et al. |
| 11,019,997 B2 | 6/2021 | Kalina, Jr. et al. |
| 11,026,860 B2 | 6/2021 | Andersen et al. |
| 11,039,958 B2 | 6/2021 | Berlin |
| 11,110,006 B2 | 9/2021 | Raksi |
| 11,147,708 B2 | 10/2021 | Horvath et al. |
| 11,166,630 B2 | 11/2021 | Frisken et al. |
| 11,173,067 B2 | 11/2021 | Raksi |
| 11,246,754 B2 | 2/2022 | Holland et al. |
| 11,316,318 B2 | 4/2022 | Yu et al. |
| 11,376,160 B2 | 7/2022 | Romano et al. |
| 11,382,794 B2 | 7/2022 | Sacks et al. |
| 11,395,765 B2 | 7/2022 | Goldshleger et al. |
| 11,399,981 B2 | 8/2022 | Fu et al. |
| 11,583,445 B2 | 2/2023 | Raksi |
| 11,612,315 B2 | 3/2023 | Delong et al. |
| 11,759,358 B2 | 9/2023 | Dorin et al. |
| 11,771,596 B2 | 10/2023 | Belkin et al. |
| 11,819,457 B2 | 11/2023 | Berlin |
| 11,826,104 B2 | 11/2023 | Kalina, Jr. et al. |
| 11,833,079 B2 | 12/2023 | Kim |
| 11,833,080 B2 | 12/2023 | Hacker et al. |
| 11,850,186 B2 | 12/2023 | Berlin |
| 11,857,463 B2 | 1/2024 | Berlin |
| 11,877,951 B1 | 1/2024 | Junger et al. |
| 2002/0013572 A1 | 1/2002 | Berlin |
| 2004/0070761 A1 | 4/2004 | Horvath et al. |
| 2006/0200113 A1 | 9/2006 | Haffner et al. |
| 2008/0058781 A1 | 3/2008 | Langeweyde et al. |
| 2009/0012507 A1 | 1/2009 | Culbertson et al. |
| 2009/0093798 A1 | 4/2009 | Charles |
| 2009/0118718 A1 | 5/2009 | Raksi et al. |
| 2009/0149840 A1 | 6/2009 | Kurtz |
| 2009/0149841 A1 | 6/2009 | Kurtz |
| 2009/0157062 A1 | 6/2009 | Hauger et al. |
| 2009/0185191 A1 | 7/2009 | Boppart et al. |
| 2010/0130966 A1 | 5/2010 | Brownell |
| 2011/0092965 A1 | 4/2011 | Slatkine et al. |
| 2011/0172649 A1 | 7/2011 | Schuele et al. |
| 2011/0202046 A1 | 8/2011 | Angeley et al. |
| 2011/0213664 A1 | 9/2011 | Osterhout et al. |
| 2011/0214082 A1 | 9/2011 | Osterhout et al. |
| 2011/0282190 A1 | 11/2011 | Caffey et al. |
| 2012/0023557 A1 | 1/2012 | Bevan et al. |
| 2012/0075168 A1 | 3/2012 | Osterhout et al. |
| 2012/0257167 A1 | 10/2012 | Gille et al. |
| 2012/0259321 A1 | 10/2012 | Vera et al. |
| 2012/0283557 A1 | 11/2012 | Berlin |

(56) References Cited

U.S. PATENT DOCUMENTS

| | | |
|---|---|---|
| 2012/0303007 A1 | 11/2012 | Loesel et al. |
| 2013/0035672 A1 | 2/2013 | Raksi |
| 2013/0085484 A1 | 4/2013 | Van Valen et al. |
| 2013/0103011 A1 | 4/2013 | Grant et al. |
| 2013/0197634 A1 | 8/2013 | Palanker et al. |
| 2013/0226160 A1* | 8/2013 | Rathjen ............... A61F 9/00831 606/4 |
| 2013/0237972 A1 | 9/2013 | Raksi |
| 2013/0289450 A1 | 10/2013 | Homer |
| 2014/0128853 A1 | 5/2014 | Angeley et al. |
| 2014/0142599 A1 | 5/2014 | Jeglorz et al. |
| 2014/0216468 A1 | 8/2014 | Goldshleger et al. |
| 2014/0236066 A1 | 8/2014 | Horvath et al. |
| 2014/0288485 A1 | 9/2014 | Berlin |
| 2014/0354951 A1 | 12/2014 | Izatt et al. |
| 2015/0077528 A1 | 3/2015 | Awdeh |
| 2015/0080783 A1 | 3/2015 | Berlin |
| 2015/0157505 A1 | 6/2015 | Neev |
| 2015/0202083 A1 | 7/2015 | Takeda et al. |
| 2015/0297408 A1 | 10/2015 | Dolzan et al. |
| 2015/0305939 A1 | 10/2015 | Vera et al. |
| 2015/0305940 A1 | 10/2015 | Vera et al. |
| 2015/0313759 A1 | 11/2015 | Vera et al. |
| 2015/0335477 A1 | 11/2015 | Schuele et al. |
| 2015/0359426 A1 | 12/2015 | Buckland et al. |
| 2016/0095751 A1 | 4/2016 | Berlin |
| 2016/0095752 A1 | 4/2016 | Srinivasan et al. |
| 2016/0213512 A1 | 7/2016 | Palanker et al. |
| 2016/0367403 A1 | 12/2016 | Siewert et al. |
| 2017/0020732 A1 | 1/2017 | Berlin |
| 2017/0027437 A1 | 2/2017 | Neal et al. |
| 2017/0042736 A9 | 2/2017 | Berlin |
| 2017/0119579 A9 | 5/2017 | Berlin |
| 2017/0127938 A1 | 5/2017 | Izatt et al. |
| 2017/0202708 A1 | 7/2017 | Berlin |
| 2017/0326003 A1 | 11/2017 | Schuele et al. |
| 2018/0028355 A1 | 2/2018 | Raksi |
| 2018/0207029 A1 | 7/2018 | Herekar et al. |
| 2018/0221205 A1 | 8/2018 | Berlin |
| 2018/0235462 A1 | 8/2018 | Gooi et al. |
| 2018/0360310 A1 | 12/2018 | Berlin |
| 2018/0360655 A1 | 12/2018 | Berlin |
| 2019/0021908 A1* | 1/2019 | Scott ....................... A61F 9/013 |
| 2019/0083313 A1 | 3/2019 | Berlin |
| 2019/0083314 A1* | 3/2019 | Berlin ................. A61F 9/00825 |
| 2019/0117459 A1 | 4/2019 | Berlin |
| 2019/0151146 A1 | 5/2019 | Kim |
| 2019/0240070 A1 | 8/2019 | Schmid et al. |
| 2019/0357768 A1 | 11/2019 | Shareef |
| 2020/0016000 A1 | 1/2020 | Raksi |
| 2020/0016002 A1 | 1/2020 | Raksi |
| 2020/0078216 A1 | 3/2020 | Raksi |
| 2020/0078217 A1 | 3/2020 | Raksi |
| 2020/0078218 A1 | 3/2020 | Holland et al. |
| 2020/0352785 A1 | 11/2020 | Holland et al. |
| 2020/0390605 A1 | 12/2020 | Raksi |
| 2020/0405542 A1 | 12/2020 | Raksi |
| 2021/0022921 A1 | 1/2021 | Berlin |
| 2021/0052416 A1 | 2/2021 | Herekar et al. |
| 2021/0186752 A1 | 6/2021 | Juhasz et al. |
| 2021/0220176 A1 | 7/2021 | Holland et al. |
| 2021/0235986 A1 | 8/2021 | Juhasz et al. |
| 2021/0298945 A1 | 9/2021 | Juhasz et al. |
| 2021/0307964 A1 | 10/2021 | Holland et al. |
| 2021/0315455 A1 | 10/2021 | Delong et al. |
| 2022/0031503 A1 | 2/2022 | Dorin et al. |

FOREIGN PATENT DOCUMENTS

| | | |
|---|---|---|
| DE | 4430720 A1 | 6/1995 |
| EP | 1080706 A1 | 3/2001 |
| EP | 1208792 A1 | 5/2002 |
| EP | 1017308 B1 | 6/2003 |
| EP | 2384727 A1 | 11/2011 |
| JP | 58187911 A | 11/1983 |
| JP | H06319765 A | 11/1994 |
| JP | 2001070337 A | 3/2001 |
| JP | 2005508704 A | 4/2005 |
| JP | 2015163193 A | 9/2015 |
| JP | 2016504964 A | 2/2016 |
| JP | 2016105827 A | 6/2016 |
| JP | 2016193033 A | 11/2016 |
| JP | 2019000742 A | 1/2019 |
| WO | 2010060443 A1 | 6/2010 |
| WO | 2013188885 A1 | 12/2013 |
| WO | 2017031570 A1 | 3/2017 |
| WO | 2018049246 A1 | 3/2018 |
| WO | 2018073625 A1 | 4/2018 |
| WO | 2018218232 A1 | 11/2018 |
| WO | 2019060756 A1 | 3/2019 |
| WO | 2019173759 A1 | 9/2019 |
| WO | 2020018242 A1 | 1/2020 |
| WO | 2022026239 A1 | 2/2022 |

OTHER PUBLICATIONS

International Written Opinion, International Patent Application No. PCT/US2020/064947, Apr. 20, 2021, 13 pgs.

Lumibird; "Optimis™ Fusion Next Generation SLY/YAG Laser"; Quantel Medical; Cournon d'Auvergne, France; 2020; 6 pgs.

Grant, "Tonographic method for measuring the facility and rate of aqueous flow in human eyes". Arch. Ophthalmol. 44(2), pp. 204-214 (1950).

Jones et al., "New methods of measuring the rate of aqueous flow in man with fluorescein". Experimental Eye Research, vol. 5:3, pp. 208-220 (Jul. 1966).

Rosenquist et al., "Ouflow resistance of enucleated human eyes at two different perfusion pressures and different extents of trabeculotomy". Current Eye Research, vol. 8:12, pp. 1233-1240 (1989).

Brubaker, "Goldmann's equation and clinical measures of aqueous dynamics". Experimental Eye Research, vol. 78, Issue 3, pp. 633-637 (2004).

Johnstone, "The aqueous outflow system as a mechanical pump: evidence from examination of tissue and aqueous movement in human and non-human primates". J Glaucoma, vol. 13:5, pp. 421-438 (Oct. 2004).

Dubbelman et al. "The shape of the anterior and posterior surface of the aging human cornea." Vision Research 46 (2006) 9931001. (Jun. 2015).

Hann et al. "Anatomic changes in schlemm's canal and collector channels in normal and primary open-angle glaucoma eyes using low and high perfusion pressures". Glaucoma, vol. 55:9 (Sep. 2014).

Kagemann et al. "Characterisation of Schlemm's canal cross-sectional area." Br J Ophthalmol 2014, 98 (Suppl. II) (Mar. 3, 2014).

McNabb et al. "Complete 360 circumferential gonioscopic optical coherence tomography imaging of the iridocorneal angle." Biomedical Optics Express vol. 6, Issue 4, pp. 1376-1391 (2015).

Slobodzian et al. "Apples to Apples: Which Camera Technologies Work Best for Beam Profiling Applications, Part 2: Baseline Methods and Mode Effects." Ophir Photonics Group. (2015.

Xin et al. "OCT study of mechanical properties associated with Trabecular meshwork and collector channel motion in human eyes." PLoS One. 2016; 11(9): e0162048. doi: 10.1371/journal.pone.0162048 (Sep. 6, 2016).

Junker et al. "Intraoperative optical coherence tomography and ab interno trabecular meshwork surgery with the trabectome." Clin Ophthalmol. 11: 17551760 (Sep. 28, 2017).

Xin et al. "Aqueous outflow regulation: optical coherence tomography implicates pressure-dependent tissue motion." Experimental Eye Research, vol. 158, pp. 171-186 (May 2017).

EP20898951.7 Partial Supplementary European Search Report (Nov. 29, 2023).

EP20898951.7 Extended European Search Report (Feb. 19, 2024).

* cited by examiner

NEAR EYE REFLECTIVE DEVICES FOR DIAGNOSTIC AND THERAPEUTIC OPHTHALMIC PROCEDURES

This application claims under 35 U.S.C. § 119(e)(1) the benefit of the filing date of, and claims the benefit of priority to, U.S. provisional application Ser. No. 62/948,227 filed Dec. 14, 2019, the entire disclosure of which is incorporated herein by reference.

BACKGROUND OF THE INVENTION

Field of the Invention

The present invention relates to systems and methods for treating the structures of the eye, including animal, mammal and human eyes. In particular, embodiments of the present inventions relate to systems and methods having reflective devices for the imaging, diagnostic and therapeutic laser operations and treatments of conditions of the eye, such as glaucoma.

The anatomical structures of the natural human eye are shown in general in FIG. 8, which is a cross sectional view of the eye. The sclera 831 is the white tissue that surrounds the lens 803 except at the cornea 801. The cornea 801 is the transparent tissue that comprises the exterior surface of the eye through which light first enters the eye. The iris 802 is a colored, contractible membrane that controls the amount of light entering the eye by changing the size of the circular aperture at its center (the pupil).

Generally, the ocular lens changes shape through the action of the ciliary muscle 808 to allow for focusing of a visual image. A neural feedback mechanism from the brain allows the ciliary muscle 808, acting through the attachment of the zonules 811, to change the shape of the ocular lens. Generally, sight occurs when light enters the eye through the cornea 801 and pupil, then proceeds through the ocular lens 803 through the vitreous 810 along the visual axis 804, strikes the retina 805 at the back of the eye, forming an image at the macula 806 that is transferred by the optic nerve 807 to the brain. The space between the cornea 801 and the retina 805 is filled with a liquid called the aqueous 817 in the anterior chamber 809 and the vitreous 810, a gel-like clear substance, in the chamber posterior to the lens.

As used herein, unless specifically stated otherwise, the term "glaucoma" should be given its broadest possible meaning and will include all conditions where the fluid transport system of the eye does not function properly, the ocular drainage pathway is blocked, restricted, damaged or otherwise not functioning, where the structures of the eye associated with fluid transport are damaged, injured or do not function properly, and where fluid pressure in the eye increases.

As used herein, unless specifically stated otherwise, the terms "beam directing device", "beam directing", "light directing", "beam path directing" and similar terms should be given their broadest possible meaning and will include reflective devices, diffractive devices, steering devices, mirrors, total internal reflection devices ("TIR"), gratings, digital micromirrors ("DM"), and micro electronic mechanical systems ("MEMS").

In general glaucoma is a group of eye diseases that damages the eye's optic nerve, resulting from a fluid buildup in the front part of your eye, i.e., posterior to the cornea and anterior to the lens. The extra fluid increases the pressure in the eye, which damages the optic nerve. There are several types of glaucoma, including for example, primary open-angle glaucoma, angle-closure glaucoma, and acute angle-closure glaucoma.

In general, primary open-angle glaucoma is the most common type of glaucoma. It happens gradually, where the eye does not drain fluid as well as it should and as a result eye pressure builds over time and starts to damage the optic nerve.

Angle-closure glaucoma (also called "closed-angle glaucoma" or "narrow-angle glaucoma") occurs when the iris is very close to the drainage angle of the eye. When this occurs, the iris can end up blocking the drainage angle. In conditions where the drainage angle gets completely blocked, eye pressure rises very quickly. This is called an acute attack, or acute angle-closure glaucoma.

The "drainage angle" or "angle" is the angle between the iris and the cornea. When the angle is open, a practitioner can see most, if not all, of the eye's drainage system by using a special mirrored lens. When the angle is narrow only portions of the drainage angle are visible, and in acute-angle closure none of it is visible.

The angle is the location where the fluid that is produced inside the eye, the aqueous humor, drains out of the eye into the body's circulatory system. One of the main structures of the drainage angle, the trabecular meshwork, plays an important role in the drainage of aqueous humor. The majority of fluid draining out of the eye is via the trabecular meshwork, then through a structure called Schlemm's canal, into collector channels, then to veins, and eventually back into body's circulatory system.

The trabecular meshwork is the spongy tissue located near the cornea through which aqueous humor flows out of the eye. The trabecular meshwork lies in the drainage angle, and 80-90 percent of aqueous humor makes its way into circulation via the trabecular meshwork and its associated structures. It is theorized that if one particular part of the trabecular meshwork is the site of greatest resistance to aqueous humor outflow, then this sight of increased outflow resistance causes the pressure increase in the eye.

Turning to FIG. 8B there is shown an eye having an open drainage angle. Turing to FIG. 8C there is shown an eye having a closed drainage angle.

Glaucoma has been be treated by using drugs, mechanical surgical procedures and both. A group of procedures, known as minimally-invasive glaucoma surgeries ("MIGS") are used to address glaucoma have been gaining acceptance and are showing good efficacy. MIGS are producers that use small devices to open up the fluid transport system of the eye and thus open the flow of the fluid from the eye.

MIGS procedures work by using microscopic-sized equipment and tiny incisions. While they reduce the incidence of complications, some degree of effectiveness is also traded for the increased safety. To the extent that small implantation devices are used with these procedures, such devices are also referred to as MIGS, or MIGS devices. The MIGS group of operations can be viewed as being divided into several categories: Miniaturized versions of trabeculectomy; Trabecular bypass operations; and Totally internal or suprachoroidal shunts. FIG. 8A shows a cross section of the eye illustrating several of these different procedures and devices. It being understood that this illustrates multiple devices for comparison purposes, and that all such devices would not be implanted in a single eye. Prior to the present inventions it is believed that there has never been a safe and effective automated laser treatment for MIGS procedures and automated laser system for MIGS procedures.

Microtrabeculectomies uses tiny, microscopic-sized tubes that can be inserted into the eye and drain fluid from inside the eye to underneath the outer membrane of the eye (conjunctiva. For example, two devices can make the trabeculectomy operation safer. These devices (the Xen Gel Stent and PRESERFLO) have shown excellent pressure lowering with improved safety over trabeculectomy in some studies.

Trabecular surgery is used because typically most of the restriction to fluid drainage from the eye rests in the trabecular meshwork. Several operations have been devised using tiny equipment and devices to cut through the trabecular meshwork without damaging any other tissues in the ocular drainage pathway. Using a special contact lens on the eye, a tiny device is inserted into the eye through a tiny incision into the trabecular meshwork under high power microscopic control. The trabecular meshwork can either be destroyed (Trabectome or Trab360) or bypassed using a tiny snorkel-like device (the iStent). These procedures are FDA-approved, but generally do not reduce the eye pressure significantly. Thus, they are typically used in early to moderate stages of glaucoma.

Suprachoroidal shunts involve using tiny tubes with very small internal openings, the front of the eye is connected to the suprachoroidal space between the retina and the wall of the eye (Glaukos shunts) to augment the drainage of fluid from the eye. This operation has relatively few serious complications and lowers pressures enough to be useful even in moderately severe glaucoma.

As used herein unless specified otherwise, the recitation of ranges of values herein is merely intended to serve as a shorthand method of referring individually to each separate value falling within the range. Unless otherwise indicated herein, each individual value within a range is incorporated into the specification as if it were individually recited herein.

Generally, the term "about" as used herein unless stated otherwise is meant to encompass a variance or range of ±10%, the experimental or instrument error associated with obtaining the stated value, and preferably the larger of these.

As used herein, unless specifically stated otherwise, the terms "femtosecond laser," "femtosecond laser beam", "femtosecond pulse", and similar such terms, are used to refer to the pulse duration, and thus also pulse length of a laser beam (which can also be referred to as pulse width), and would mean all lasers and laser beams with pulse durations of less than 1 picosecond (less than $1 \times 10^{-12}$ seconds) to and including 1 femtosecond (fs) ($1 \times 10^{-15}$ seconds).

As used herein, unless specifically stated otherwise, the terms "picosecond laser," "picosecond laser beam", "picosecond pulse", and similar such terms, are used to refer to the pulse duration, and thus also pulse length of a laser beam, (which can also be referred to as pulse width) and would mean all lasers and laser beams with pulse durations of 1 picosecond (ps) ($1 \times 10^{-12}$ seconds) up to 1 nanosecond (ns) ($1 \times 10^{-9}$ seconds).

In general, therapeutic laser procedures for the eye involve positioning the patient on a bed, or patient support, aligning the eye with the laser beam path of the laser system and attaching a patient interface device ("PID") between the laser system and the eye. The therapeutic laser beam is then delivered in a laser beam pattern to perform a therapeutic laser operation on the eye, and in particular, the structures of, or associated with the eye to address conditions of the eye.

While various hand-held laser procedures have been tried, to address glaucoma they are generally viewed as having less than optimum outcome in typical cases. Prior to the present inventions, it is believed that no one has had an automated, or fully automated laser delivery system, where a predetermined therapeutic laser beam pattern was delivered to a predetermined targeted location in the eye for treating glaucoma, and other conditions of the eye in the annular area where the cornea and iris meet.

One of the major problems with using automated laser systems in treating glaucoma is the interference from the PID. The PID is the device that is placed on the eye, typically applies a ring of suction to attach to the eye, and then mechanically, i.e., physically, docks with the laser system. Imaging, diagnostic and therapeutic laser beam paths and light are delivered through the PID and images of the structures of the eye are transmitted through the PID to the laser system, cameras and microscopes, as well as, other devices. While providing sufficient field of view, and opening, for delivery of the laser beams to the cornea and the lens of the eye, i.e., for refractive surgery and cataract surgery, they have been wholly inadequate for use in the treatment of glaucoma, and for structures of the eye, located in the annular area where the cornea and iris meet including the trabecular meshwork. Prior to the present inventions, the PIDs blocked and obstructed the ability to have imaging, therapeutic or diagnostic laser beams delivered to the annular area where the iris and cornea meet. Generally, prior laser PIDs blocked the field of view, and laser beam paths, to this area of the eye.

This Background of the Invention section is intended to introduce various aspects of the art, which may be associated with embodiments of the present inventions. Thus, the forgoing discussion in this section provides a framework for better understanding the present inventions, and is not, and should not be viewed as, an admission of prior art.

SUMMARY

There exists a long standing and unfulfilled need to improve the safety and efficacy, as well as, surgeon to surgeon uniformity, of the treatment of glaucoma, and other conditions of the eye. There exists a long standing and developing need to improve the effectiveness of MIGS. The present inventions, among other things, solve these and other needs by providing the articles of manufacture, devices and processes set forth in this specification, drawings and claims.

Thus, there is provided a laser system for treating conditions of the eye, the laser system having: a therapeutic laser beam for providing a therapeutic laser beam a long a laser beam path; a beam directing device located near the surface of the eye.

Further there is provided a method of delivering a therapeutic laser beam to a structure of the eye, including directing the laser beam along a laser beam path that forms an angle from 15 to 120 degrees with the optical axis of the eye.

Additionally, there is provided a laser system for imaging of the eye, the laser system having: a light source for illuminating the eye and a light path for providing images of the eye to an image processor; a light directing device located near the surface of the eye; wherein the light path for the image forms an angle from 15 to 120 degrees with the optical axis of the eye.

Still further there is provided a method of receiving images from the eye, having directing an illumination source to a structure of the eye, and receiving an image for the illuminated structure of the eye along an optical path that forms an angle from 15 to 120 degrees with the optical axis of the eye.

Moreover, there is provided a laser system for treating conditions of the eye, the laser system having: a therapeutic laser for providing a therapeutic laser beam a long a laser beam path; and, a near eye beam directing device having a beam director; wherein the near eye beam directing device is configured when in operation to maintain the beam director less than about 5 mm above a surface of an eye.

There is further provided one or more of these systems, devices and methods having one or more of the following features: wherein the near beam directing device is configure to provide a laser beam path having a beam path angle of about 25° to 65°; wherein the near beam directing device is configure to provide a laser beam path having a beam path angle of about 35° to 55°; wherein the near beam directing device is configure to provide a laser beam path having a beam path angle of about 45° to 75°; wherein the beam director has a MEMS; wherein the beam director has a DM; wherein the beam director is a TIR device; wherein the near eye beam directing device is mechanically engaged with the laser system; wherein the laser system has a laser delivery head and the near eye beam directing device is mechanically engaged with the laser delivery head; wherein the near eye beam directing device is configured for engagement with the eye; wherein the near eye beam directing device is configured when in operation to maintain the beam director less than about 2.5 mm above a surface of an eye; wherein the near eye beam directing device is configured when in operation to maintain the beam director less than about 1 mm above a surface of an eye; and, wherein the near eye beam directing device is configured when in operation to maintain the beam director less than about 0.5 mm above a surface of an eye.

Yet additionally, there is provided a laser system for treating conditions of the eye, the laser system having: a therapeutic laser for providing a therapeutic laser beam a long a laser beam path; and, a near eye beam directing device having a beam director; wherein the near beam directing device is configure to provide a laser beam path having a beam path angle of greater than about 25°; and, wherein the near beam directing device is configure to provide a laser beam path that contact an area of the eye where an iris and a cornea meet.

Additionally, there is provided a laser system for treating conditions of the eye, the laser system having: therapeutic laser beam for providing a therapeutic laser beam a long a laser beam path; a near eye beam directing device having a beam director; and, a predetermined laser beam pattern configured for the delivery of a laser beam to an area of the eye where an iris and a cornea meet.

Still further there is provided a laser system for treating conditions of the eye, the laser system having: therapeutic laser beam for providing a therapeutic laser beam a long a laser beam path; a near eye beam directing device having a beam director; and, a predetermined laser beam pattern configured to direct the laser beam path to contact an area of the eye where an iris and a cornea meet.

Additionally, there is further provided one or more of these systems, devices and methods having one or more of the following features: wherein the predetermined laser beam pattern is configured to open a drainage angle of an eye; wherein the predetermined laser beam pattern is configured to provide for the removal of tissue in the area of the eye where the iris and the cornea meet; whereby a MIGS device can be implanted; wherein the predetermined laser beam pattern is configured for a MIGS procedure; wherein the near beam directing device is configure to provide a laser beam path having a beam path angle of about 25° to 65°; wherein the near beam directing device is configure to provide a laser beam path having a beam path angle of about 35° to 55°; wherein the near eye beam directing device is configured when in operation to maintain the beam director less than about 10 mm above a surface of an eye; wherein the near eye beam directing device is configured when in operation to maintain the beam director less than about 5 mm above a surface of an eye; wherein the near eye beam directing device is configured when in operation to maintain the beam director less than about 1 mm above a surface of an eye; wherein the beam director has a MEMS; wherein the beam director has a DM; wherein the beam director is a TIR device; wherein the near eye beam directing device is mechanically engaged with the laser system; wherein the laser system has a laser delivery head and the near eye beam directing device is mechanically engaged with the laser delivery head; wherein the near eye beam directing device is configure to provide a laser beam path having a beam path angle of about 35° to 55°; and, wherein the near eye beam directing device is configured for engagement with the eye.

Moreover, there is provided a method of delivering a therapeutic laser beam to a structure of the eye, having: directing the therapeutic laser beam laser beam along an incoming laser beam path to a director device, whereby the laser beam leaves the director device traveling along a directed laser beam path, wherein the directed beam path forms a beam path angle that is greater than about 25°; and wherein the directed beam path contacts an area of the eye selected from the group consisting of the area where the iris and cornea meet, the drainage angle, and the trabecular meshwork.

Still further, there is provided one or more of these systems, devices and methods wherein the system is configured to provide images of an area of the eye selected from the group consisting of the area where the iris and cornea meet, the drainage angle, and the trabecular meshwork, along the laser beam path.

Still further, there is provided one or more of these systems, devices and methods wherein the system is configured to provide images of an area of the eye selected from the group consisting of the area where the iris and cornea meet, the drainage angle, and the trabecular meshwork, along the laser beam path; wherein images of the area of the eye selected from the group consisting of the area where the iris and cornea meet, the drainage angle, and the trabecular meshwork, along the laser beam path and transmitted along the incoming coming laser beam path, the directed laser beam path or both.

Additionally, there is provided a near eye beam directing device comprising: a beam director; wherein the near eye beam directing device is configured to maintain the beam director less than about 5 mm above a surface of an eye; and wherein the beam director is configured to receive an incoming laser beam along an incoming laser beam path from a therapeutic laser and provide a directed laser beam along an outgoing laser beam path; wherein in operation the directed laser beam path forms a beam path angle, wherein the beam path angle is greater than about 25°.

Still further, there is provided one or more of these systems, devices and methods having one or more of the following features: wherein the near beam directing device is configure to provide a laser beam path having a beam path angle of about 30° to 75°; wherein the near beam directing device is configure to provide a laser beam path having a beam path angle of about 35° to 65°; wherein the near beam directing device is configure to provide a laser beam path having a beam path angle of about 30° to 55°; and, wherein the near beam directing device is configure to provide a laser beam path having a beam path angle of about 40° to 70°.

There is also provided a laser system for treating conditions of the eye, the laser system having a therapeutic laser for providing a therapeutic laser beam along a laser beam path; a device for determining a shape and position of a structure of an eye; a control system comprising a predetermined MIGS procedure laser shot pattern; wherein (i) the device for determining the shape and position of the structure of the eye and (ii) the therapeutic laser for providing the therapeutic laser beam are in control communication with the control system; a near eye beam directing device comprising a beam director; wherein the near eye beam directing device is configure to provide a laser beam path having a beam path angle of greater than about 25¬ƒ; and, wherein the near eye beam directing device, the control system and the device for the determining the shape and position of the structure of the eyer are configured to provide the therapeutic laser beam in the predetermined MIGS procedure laser shot pattern along the laser beam path to an area of the eye where an iris and a cornea meet.

Additionally, there is further provided one or more of these systems, devices and methods having one or more of the following features: wherein the device for determining the shape and position of the eye is selected from the group consisting of an OCT device and a Scheimpflug device; wherein the area of the eye is selected from the group consisting of a drain angle and a trabecular mesh; and, wherein the beam director comprises a device selected from the group comprising a MEMS, a DM and a TIR device.

Yet additionally, there is provided a laser system for treating conditions of the eye, the laser system having: therapeutic laser beam for providing a therapeutic laser beam along a laser beam path; a device for determining a shape and position of a structure of an eye; a control system comprising a predetermined laser beam pattern configured for the delivery of a laser beam to an area of the eye where an iris and a cornea meet; and, a near eye beam directing device comprising a beam director.

Moreover, there is provided one or more of these systems, devices and methods having one or more of the following features: wherein the predetermined laser beam pattern comprises a MIGS procedure laser shot pattern; wherein the device for determining the shape and position of the eye is selected from the group consisting of an OCT device and a Scheimpflug device; wherein the structure of the eye is selected from the group consisting of a drain angle and a trabecular mesh; and, wherein the area of the eye is selected from the group consisting of a drain angle and a trabecular mesh; wherein the beam director selected from the group consisting of a micro electrical mechanical system, a MEMS, a DM, a TIR device, a plurality of MEMS, a plurality of micro electrical mechanical system, a plurality of DMs and a plurality of TIR devices; and, wherein (i) the device for determining the shape and position of the structure of the eye and (ii) the therapeutic laser for providing the therapeutic laser beam are in control communication with the control system.

Additionally, there is provided an automated method, and systems that automatically perform this method, of delivering a therapeutic laser beam to a structure of the eye, the method including: determining a position of a drain angle of the eye, a trabecular mesh of the eye or both to thereby define a determined location; directing the therapeutic laser beam laser beam along an incoming laser beam path to a director device, whereby the laser beam leaves the director device traveling along a directed laser beam path, wherein the directed laser beam path forms a beam path angle that is greater than about 25-J; and wherein the directed laser beam path contacts the determined location, whereby the therapeutic laser beam is delivered to the determined location, to thereby in part open a drain angle of the eye.

There is further provided one or more of these systems, devices and methods having one or more of the following features: wherein the position of the director device is located; wherein the position, location, or both of the director device with respect to the laser, the incoming beam path, or both, is determined by the device for determining a shape and position of a structure of an eye; wherein the position, location, or both of the director device with respect to the laser, the incoming beam path, or both, is determined by an OCT device; and, wherein the position, location, or both of the director device with respect to the laser, the incoming beam path, or both, is determined by a Scheimpflug device.

DESCRIPTION OF THE PREFERRED EMBODIMENTS

Figure 1:
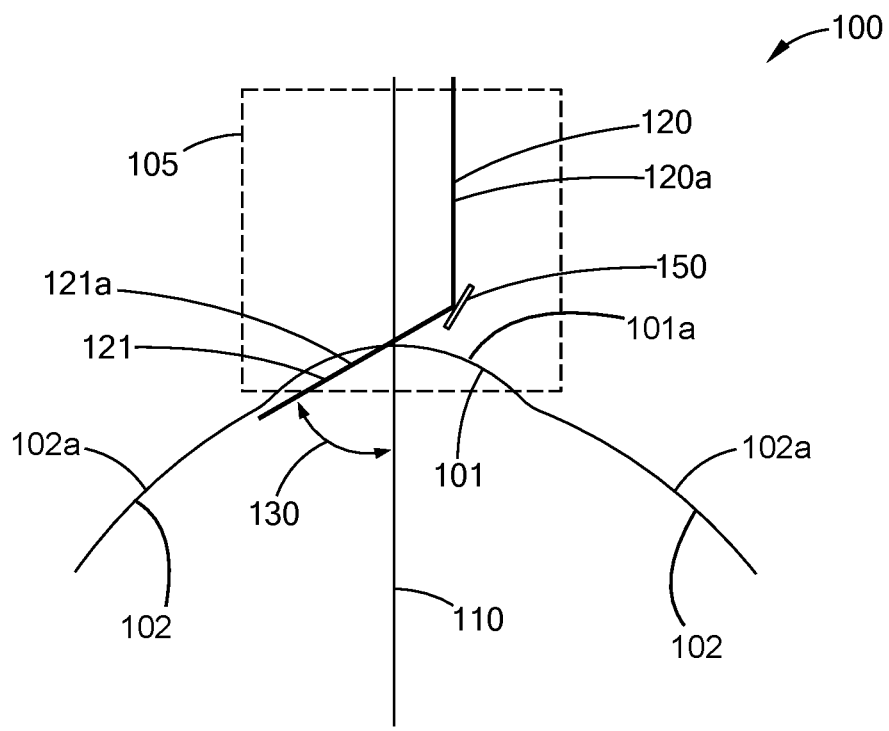
FIG. 1 is a cross sectional schematic view of an embodiment of a system for directing laser beams in accordance with the present inventions.

In general, embodiments of the present inventions provide systems and methods for addressing conditions of the eye, including the diseases of the eye, such as glaucoma. In particular, embodiments of the present inventions provide devices, systems and methods for imaging, diagnosis and therapies to, and for, the area of the eye where the cornea and iris meet, including the drainage angle and the trabecular meshwork.

In general, embodiments of the present inventions relate to laser eye surgery systems, of the type generally used for refractive surgery and cataract surgery. In general, in embodiments of the present inventions, the laser beam paths and the image paths, and thus the laser beams, laser beam patterns, images and light traveling along those paths, is reflected, diffracted, directed or steered near the front surface of the eye. Generally, a device to reflect, diffract, direct or steer the laser beams and light is positioned near, on or in the eye.

Generally, this device provides for laser beam paths that form an angle to the optical axis of the eye, e.g., the angle formed by the beam path, laser or light, as it crosses or with respect to the optical axis, of about 5° to about 120°, about 25° to about 90°, about 35° to about 60°, about 5°, about 15°, about 25°, about 45°, about 60°, and combinations and variations of these angles as well as larger and smaller angles. Generally, this device can be located on the surface of the eye, such as in an applanator or contact lens, it can be located from 0 mm to about 5 cm above the surface of the eye, it can be located from 0.2 mm to about 20 mm above the surface of the eye, it can be located from 0.5 mm to about 15 mm above the surface of the eye, it can be located from 0.5 mm to about 5 mm above the surface of the eye, it can be located from 1 mm to about 5 mm above the surface of the eye, it can be located from 0.2 mm to about 2.5 mm above the surface of the eye, it can be located from 0 mm to about 2 cm above the surface of the eye, it can be located less than about 3 cm above the surface of the eye, it can be located less than about 2 cm above the surface of the eye, it can be located less than about 1 cm above the surface of the eye, it can be located less than about 8 mm above the surface of the eye, it can be located less than about 5 mm above the surface of the eye, it can be located less than about 3 mm above the surface of the eye, it can be located less than about 2 mm above the surface of the eye, Combinations of each of these locations for the device and changes in the angle of paths from the optical axis are contemplated.

Although the present specification focusses on glaucoma, the drainage angle, the trabecular meshwork, and improving the drainage of aqueous humor, it should be understood that the present devices and systems provide greater overall access to, visibility of, and beam paths to, all structures within the eye, and thus, find applications in other procedures and to address conditions of the eye in addition to glaucoma.

Turning to FIG. 1 there is shown a cross section schematic of an embodiment of a system for having laser beam and image paths, and for delivering laser beams and receiving images along those paths of the structures where the iris and cornea meet, the drainage angle, and the trabecular meshwork. The near eye beam directing system 100, is shown with respect to the cornea 101 of an eye, the cornea having an outer surface 101a, and the sclera 102 of the eye, the sclera 102 having an outer surface 102a. The beam directing device 150, i.e., a beam director, is located generally in area 105, which is near to the surface of the eye, and in particular near to the surface of the cornea 101a. The beam directing device receives incoming light, e.g., an incoming laser beam 120 (therapeutic, imaging, diagnostic, etc.) along a laser beam path 120a (the beam and beam paths are coincident) from the laser beam source, i.e., a laser (not shown). The beam directing device 150 changes the direction of the laser beam 120a to a new path, which is the directed laser beam path 121a that the directed laser beam 121 travels along. The directed laser beam 121 and directed laser beam path 121a form angle 130 (the "beam path angle") with the optical axis 110 of the eye at the final point where the laser beam and beam path cross the optical axis.

In the various embodiments of this Specification the beam path angle (as measure in FIG. 1, item 130) created by the near eye directing system can be about 5° to 75°, 25° to 65°, about 35° to 60°, about 45°, about 50°, about 55°, about 65° and larger and smaller angles, as well as all angles within those ranges.

In embodiments the beam path angle can be such that the device is configure so that in operation the beam path, and thus laser beam traveling along the path, contacts the area of the eye where the iris and cornea meet, and the beam path angle is greater than about 25°, greater than about 30°, greater than about 35°, greater than about 40°, and greater than about 45°.

The beam directing device 150 can be any of the of the devices and systems discussed in the Beam Directing Devices and Sub-Systems—General teachings, and can be reflective devices, diffractive devices, steering devices, mirrors, total internal reflection devices ("TIR"), gratings, digital micromirrors ("DM"), and micro electronic mechanical systems ("MEMS"), as well as other devices and systems that can steer or redirect the laser beam or light.

The beam directing device 150 can be located: in a contact lens; on a contact lens; in an applanation device (curved or flat); on an application device (curved or flat); as part of a PID, including the wall, entrance, side, top or bottom, and as part of a multicomponent PID; and, as part of a suction ring which does not dock with a laser system. Combinations and variations of these and other ways in which to affix, position or hold, the beam directing device in the area 105, in a fixed position with respect to the eye, and both are contemplated.

Figure 2:
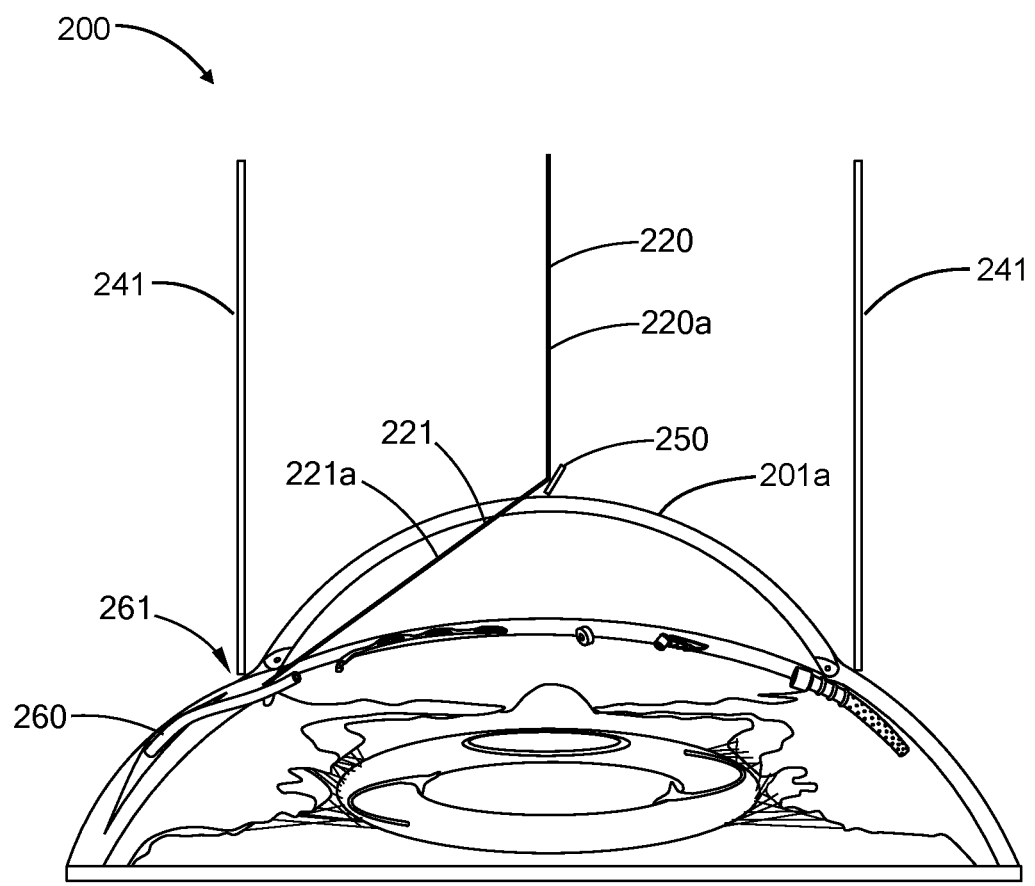
FIG. 2 is a perspective cross sectional view of an embodiment of a system for directing laser beams in accordance with the present inventions.

Turning to FIG. 2 there is shown a perspective view of the structures of an eye and a near eye beam directing device 200. The near eye beam directing device 200 has a beam directing device 250 located near the surface of the cornea 201a, within the inner structures 241 of a PID, e.g., walls of the PID (it being understood that the outer and other structures of the PID are not shown in the figure). The incoming laser beam 220 travels along incoming beam path 220a to contact beam directing device 250. Directed laser beam 221 leaves the beam directing device 250 traveling along directed laser beam path 221a. The directed laser beam 221 is directed to the area 261 where the drainage angle and trabecular mesh are located. Once the laser procedure is performed at area 261 by the directed laser beam 221, which may have a predetermined laser beam pattern, an implantation device, e.g., a MIGS device 260 can be implanted. In other laser operations, an implantation device may not be needed or used. In is noted that FIG. 2 shows other types and locations of MIGS devices, which may also be implanted by the present embodiment.

Thus, the laser operation using the near eye beam directing device 200 can be performed at the areas where those other devices are shown in FIG. 2, which overall area is understood to be the annular area the iris and cornea meet, the drainage angle is located, and the trabecular meshwork is located. It being understood that the illustration of multiple implantation devices, e.g., MIGS devices, is only to show that other types of implantation devices may be used with the present laser devices, system and methods. Typically, only one, or at times two implantation devices may be used, although at times more may also be used.

As discussed in this specification for all laser beam paths, it is understood that light can travel in both directions along a laser beam path. Thus, light used for the determination of the shape and position of structures, such as the drainage angle and trabecular mesh, may travel down and back along the directed laser beam path (e.g., 221a) and the incoming laser beam path (e.g., 220a).

It is further understood that the laser operations and imaging, are preferably configured for full 360° operation. Thus, imaging and laser operations can be performed around the entire circumference of the drainage angle, and the trabecular mesh; and, the general annular area or location defined by where the the iris and cornea meet.

Therapeutic Laser and System—Generally

Any laser that is configured to provide a laser beam that is useful, safe and effective for treating the eye, its structures and adjacent tissues, and conditions thereof, can be used to provide a therapeutic laser beam. The therapeutic laser can be a pulsed laser, such as femto second laser or a pico second laser, and longer and shorter pulses, a continuous laser and combinations of these.

The therapeutic laser can have a wavelength in the IR spectrum, the UV spectrum, as well as other wavelengths. The therapeutic laser beams can have wavelengths of from about 300 nanometers (nm) to about 2,500 nm, from about 1,000 to about 1,300 nm, 1020 nm, about 1020 nm, 1030 nm, about 1030 nm, 1040 nm, about 1040 nm, 1050 nm, about 1050 nm, and from about 1020 to about 1050 nm, and combinations and variations of these as well as other wavelengths.

The therapeutic laser can have pulse durations of from about 1 fs to about 100 ps, from about 200 fs to about 500 ps, from about 500 fs to about 5 ps, from about 300 fs to about 100 ps, from about 300 fs to about 10 ps, from about 300 fs to about 2,000 fs, and combinations and variation of these wavelengths, as well as longer and shorter durations.

The therapeutic laser beams can average output power at a specified pulse repetition rate of from about 1 Watt (W) to about 8 W, from about 2.5 W to about 5 W, from about 3 W to about 4.5 W, from 3 W to 5 W, less than 6 W, less than 5 W, any power where laser induced optical breakdown (LIOB), photodisruption or both occurs and combinations and variations of these, and lower and higher powers.

The therapeutic laser beams can have a pulse energy of from about 1 nanojoule (nJ) to about 1 millijoule (mJ), from about 2 microjoules (µJ) to about 70 µJ, from about 5 µJ to about 45 µJ, from about 2 µJ to about 35 µJ, from about 10 µJ to about 30 µJ, less than 45 µJ, less than 35 µJ, any pulse energy where photodisruption, LIOB or both occurs, and combinations and variations of these, and lower and higher energies.

The therapeutic laser beams of the present systems can have one or more of the above beam features, e.g., wavelength, duration, repetition rate, power, and pulse energy, and combinations and variations of these.

A wide variety of laser types may be used to have a therapeutic effect, e.g., cause photodisruption, LIOB or both of ocular tissues, dependent upon pulse length and energy density, as well as other factors. Thus, examples of such lasers would include: Titanium Sapphire (Ti:Sapphire); FCPA (fiber chirped pulse amplification); an Yb:fiber oscillator/amplifier a Nd:YVO4; These and other similar lasers may be used a therapeutic laser and to generate therapeutic laser beams.

The therapeutic lasers and laser beams can be of the type used for SLT (selective laser trabeculoplasty); or those used for argon laser trabeculoplasty. An example of an SLT laser would be a 533 nm (Q-switched, frequency doubled Nd:YAG), having an energy level of 0.3 to 2 mJ, a pulse duration of 4 ns and a 400 micron spot size, and a repetition rate of 2.5 Hz. An example of a laser for argon laser trabeculoplasty is a continuous 455-529 nm wavelength argon laser.

Embodiments of laser systems, methods and apparatus for performing laser operations on the eye are disclosed and taught in US patent application Publication Nos. 2016/0302971, 2015/0105759, 2014/0378955, and U.S. Pat. Nos. 8,262,646 and 8,708,491, the entire disclosures of each of which are incorporated herein by reference.

Laser Beam Delivery—Generally

In general, embodiments of the optics for delivering the therapeutic laser beam to the structures of the eye, including the drain angle, trabecular mesh and the area of, or location in, the eye where the iris and cornea meet, should be capable of providing a series of laser shots to those structures in a precise and predetermined pattern in the x, y and z dimension. The optics should also provide a predetermined beam spot size to cause photodisruption, LIOB or both with the laser energy reaching those structures or other targeted tissue. Thus, the optics may include, without limitation: an x y scanner; a z focusing device; and, focusing optics. The focusing optics may be conventional focusing optics, and/or flat field optics and/or telecentric optics, each having corresponding computer controlled focusing, such that calibration in x, y, z dimensions is achieved. For example, an x y scanner may be a pair of closed loop galvanometers with position detector feedback. Examples of such x y scanners would be the Cambridge Technology Inc. Model 6450, the SCANLAB hurrySCAN and the AGRES Rhino Scanner. Examples of such z focusing devices would be the Phsyik International Peizo focus unit Model ESee Z focus control and the SCANLAB varrioSCAN.

The therapeutic laser beam path, the shape and position deterring laser beam or light paths, and image light paths may be coincident along some or all of the length of their beam paths. They may share some or all of the optics along one or more of the beam paths.

Laser Control System—Generally

In general, embodiments of the control system for delivering the therapeutic laser beam may be any computer, controller, and/or software hardware combination that is capable of selecting and controlling x y z scanning parameters and laser firing, among other things. These components may typically be associated at least in part with circuit boards that interface to the x y scanner, the z focusing device and/or the laser. Among other things, the laser control system may contain the programs that direct the laser through one or more laser shot patterns. The laser control system can also control other components of the system, as well as, maintaining data, obtaining data, analyzing data and images, preparing and suggesting table and treatments, and performing calculations. The control system may contain the programs that direct the laser beam through one or more laser shot patterns.

Position and Shape Determination—Generally

In general, in embodiments, the assembly or device for determining the shape and position of the eye and structures within the eye, including the drain angle, trabecular mesh and the area of, or location in, the eye where the iris and cornea meet, can be an optical coherence tomography (OCT), a Scheimpflug device having movable, multiple and both cameras, and other types of devices for making such determinations. This device, in embodiments should be capable of determining the relative distance with respect to the laser and portions of the lens, or other structures of the eye or tissue adjacent to the eye, which distance is maintained constant by for example the PID. Thus, this device can provide the ability to determine the position of the lens, the cornea, the drain angle, the trabecular mesh, the location where the iris and cornea meet, and other structures, with respect to the scanning coordinates in all three dimensions. This may be accomplished by several methods and apparatus. For example, x y centration of the lens may be accomplished by observing the lens through a co-boresighted camera system and display or by using direct view optics and then manually positioning the patients' eye to a known center. The z position may then be determined by a range measurement device utilizing optical triangulation or laser and ccd system, such as the Micro-Epsilon opto NCDT 1401 laser sensor and/or the Aculux Laser Ranger LR2-22. The use of a 3-dimensional viewing and measurement apparatus may also be used to determine the x, y and z positions of the drain angle, trabecular mesh and the area of the eye where the iris and cornea meet. For example, the Hawk 3 axis non-contact measurement system from Vision Engineering could be used to make these determinations. Yet a further example of an apparatus that can be used to determine the position of the lens is a 3-dimension measurement apparatus. This apparatus would comprise a camera or cameras, which can view a reference and the natural lens, and would also include a light source to illuminate the natural lens. Such light source could be a structured light source, such as for example a slit illumination designed to generate 3-dimensional information based upon geometry. Further one, two, three, four or more, light sources can be positioned around the eye and the electronically activated to provide multiple views, planar images, of the eye, and in particular the cornea and the lens, at multiple planar slices that can them be integrated to provide data for position and location information relative to the laser system about those structures. A surgical microscope may also be used, and may be used in conjunction with these other apparatus to determine the shape and position of structures of the eye.

Another embodiment for a shape and position determining system is a structured light illumination sub-system arranged with the structured light illumination source, the structured light camera and the lens for the structured light camera in the so-called Scheimpflug configuration which is well-known. In summary, the Scheimpflug condition states that given an object, a lens and an image, that the object plane is imaged sharply in the image plane if the object plane, the lens plane and the image plane intersect in the same line. The structured light source projects a line and or a plurality of lines onto the eye at an angle or plurality of angles. The light scattered at the eye lens forms the object to be imaged by the lens and focused onto the camera system. Since the slit illuminated image in the eye may be at a large angle with respect to the camera lens and camera, this presents a large depth of field to the camera and the entire slit image may not be in sharp focus at the camera. By tilting the camera lens and the camera at an angle or plurality of angles such that Scheimpflug's condition is met, the image along the illuminated plane can be in sharp focus. Alternately, the camera and/or lens may be tilted such that the angle between the slit illuminated image plane and the camera focal plane is reduced, improving the depth-of-focus sharpness, however may not meet the Scheimpflug condition. Such configurations can improve sharpness further by reducing the aperture of the optical path, thereby increasing the F # of the system. These angles will depend on the angle the slit beam makes with the eye. This will increase the depth of field at the object, the scattered light from the slit illuminator, and allow it to imaged through the lens onto the camera image plane and remain in focus for the entire depth of the object.

The structured light illuminating and receiving system may be contained within the surgical laser system or it may be a separate unit for evaluating the suitability of a candidate patient for laser lens surgery. Commercially available examples of such structured light illuminating and receiving systems are the Ziemer Ophthalmic Systems GALILEI Dual Scheimpflug Analyzer and the Oculus, Inc. PENTACAM. It is believed that these systems cannot be used to determine the position of the lens with respect to the treatment laser. However, lens shape data from these systems may be obtained and then used in conjunction with position data provided by systems such as the position determining systems described in this specification.

Examples of assemblies, methods, devices for determining the shape and position of the eye and structures, with respect to the laser, laser shot pattern, and laser beam, are disclosed and taught in US patent publications and patents numbers 2018/0085256, 2016/0302971, 2015/0105759, 2012/0330290, 2016/0030244, U.S. Pat. Nos. 9,180,051 and 8,708,491, the entire disclosure of each of which is incorporated herein by reference.

Patient Interface Devices—Generally

A further component of embodiments of these systems can be the laser patient interface or PID. It is noted that all or some of the PID is typically not a part of the laser system, but is preferably a one-time use device, that is added to the system for each patient prior to, or as set up for, a laser procedure. The PID may also be a multi-part device, having a one time use component and a reusable component. In embodiments, this interface provides that the x, y, z position between the target tissue, including the drain angle, trabecular mesh and the area of the eye where the iris and cornea meet, and the laser remains fixed during the procedure, which includes both the measurement steps of determining the x y z position and the delivery step of delivering the laser to the lens in a shot pattern. The interface device may contain an optically transparent applanator. One example of this interface is a suction ring applanator that is fixed against the outer surface of the eye and is then positioned against the laser optical housing, thus fixing the distance between the laser, the eye and the natural lens. Reference marks for the 3-dimensional viewing and measuring apparatus may also be placed on this applanator. Moreover, the interface between the lower surface of the applanator and the cornea may be observable and such observation may function as a reference. A further example of a laser patient interface is a device having a lower ring, which has suction capability for affixing the interface to the eye. The interface further has a flat bottom, which presses against the eye flattening the eye's shape. This flat bottom is constructed of material that transmits the laser beam and also preferably, although not necessarily, transmits optical images of the eye within the visible light spectrum. The upper ring has a structure for engaging with the housing for the laser optics and/or some structure that is of known distance from the laser along the path of the laser beam and fixed with respect to the laser. Examples of patient interfaces devices, and system to engage the PID with the eye, are disclosed and taught in US Patent Application Publication Nos. 2017/0290703, 2010/0022994, 2011/0022035 and 2015/0088175, the entire disclosures of each of which are incorporated herein by reference.

Beam Directing Devices and Sub-Systems—Generally

In general, the beam directing device for use in the near eye beam directing device can be reflective devices, diffractive devices, and steering devices, of any type. These devices can be gratings or other similar structures that are incorporated into optical blocks or optical structures that are transparent to the therapeutic laser beam, the laser beam or light used for position and shape determination and light of imaging. Thus, in an embodiment the beam directing device is incorporated into an optical block, hard contact lens, or similar structure. The beam directing device can be affixed to or a part of the end of an optical fiber or fibers. The beam directing device can be a mirror. The beam directing device can be a reflecting device that is based upon total internal reflection ("TIR") and thus would be a TIR device.

The beam directing devices can be a micro electronic mechanical systems ("MEMS"). The devices can be less than 1 mm in size (largest dimension), less than 0.5 mm, less than 0.01 mm, and in the micron sizes, e.g., 1 to 10 microns and combinations and variations of these and larger and smaller sizes. MEMS that is usefully for the present inventions are digital micromirrors ("DM"). Other micro electrical mechanical systems that can steer or redirect the laser beam can also be used. One, two, five, ten, tens, hundreds, and thousands (depending on the size) or these micro devices, and combinations and variations of these, can be used to, or can make up, the beam directing device.

These beam directing devices can be located anywhere along the laser beam(s) path, e.g., the therapeutic laser beam path, the shape and position deterring laser beam or light paths, and image light paths. Preferably all beam paths intersect the beam deflecting device. Preferably the beam deflection device is near the surface of the eye.

The systems may have one, two, three, four, five or more beam directing devices. The beam directing devices may be arranged in a circular configuration to form a ring. They may be a bar structure, a linear structure, a curved structure, or arranged in other configurations and shapes.

Thus, by way of example, the beam directing device can be located in a contact lens as for example a grating or optical structure formed within the contact lens material. The beam directing device can be located on a contact lens. The beam directing device can be located in an optical block, such as an applanator, as for example a grating or optical structure formed within the optical block. The optical block can be curved or flat. The beam directing device can be a part of the PID. In this embodiment, for example, the beam directing device can be positioned along the inner wall or surface of the PID. It can be positioned at the entrance or bottom of the PID. The beam directing device can be fixed with respect to the PID or it can be movable with respect to the PID. The beam directing device can be a separate module that is a part of the PID. Combinations and variations of these configurations are contemplated.

The beam directing device can be part of, or held by a suction ring, which does not dock with a laser system.

Combinations and variations of the forgoing and other ways in which to affix, position or hold, the beam directing device in the area near or on the surface of the eye may be used.

The beam directing device can be a DM. In an embodiment of the DM, there one, two, three, ten, tens, hundreds of micro mirrors. Each mirror mounted is suspended yoke with the torsion spring with the electrostatic pads of the memory cells below. In an embodiment the mirrors themselves are made out of aluminum and are around 16 micrometers across. Each one is mounted on a yoke which in turn is connected to two support posts by compliant torsion hinges. In this type of hinge, the axle is fixed at both ends and twists in the middle. Because of the small scale, hinge fatigue is not a problem.

Two pairs of electrodes control the position of the mirror by electrostatic attraction. Each pair has one electrode on each side of the hinge, with one of the pairs positioned to act on the yoke and the other acting directly on the mirror. The majority of the time, equal bias charges are applied to both sides simultaneously. Instead of flipping to a central position as one might expect, this actually holds the mirror in its current position. This is because attraction force on the side the mirror is already tilted towards is greater, since that side is closer to the electrodes.

To move the mirrors, the required state is first loaded into an SRAM cell located beneath each pixel, which is also connected to the electrodes. Once all the SRAM cells have been loaded, the bias voltage is removed, allowing the charges from the SRAM cell to prevail, moving the mirror. When the bias is restored, the mirror is once again held in position, and the next required movement can be loaded into the memory cell.

The bias system is used because it reduces the voltage levels required to address the pixels such that they can be driven directly from the SRAM cell, and also because the bias voltage can be removed at the same time for the whole chip, so every mirror moves at the same instant. The advantages of the latter are more accurate timing and a greater moving image range.

An example of a DM is the Digital Micromirror Device™ (DMD™) by Texas Instruments (TI), first conceived in the 1980s (Hornbeck, 1996). It consists of an array of micromirrors, each on the order of 10 μm in width with an individually controllable tilt degree of freedom.

Smith, et. al, Single chip Lidar with discrete beam steering by digital micromirror device, Vol. 25 Issue 13, pp 14732-14747 (Optics Express 2017); Benton, Multiple beam steering using dynamic zone plates on a micro-miror arry, Optical Engineering, 57(7), (Jul. 27, 2018); Davis, Optical MEMS for displays in portable systems, Handbook of Mems for Wireless and Mobile Applications (2013) contain general teachings and disclosures for MEMS, each of which is incorporated by reference into this specification in its entirety. MEMS can be used as the beam directing devices, and in embodiments MEMS are the preferred beam directing device in a near eye beam directly system.

EXAMPLES

The following examples are provided to illustrate various embodiments of systems, processes, compositions, applications and materials of the present inventions. These examples are for illustrative purposes, may be prophetic, and should not be viewed as, and do not otherwise limit the scope of the present inventions.

The embodiments of these Examples 1 to 5 can have or utilize one or more of the embodiments, processes, methods, features, functions, parameters, components, or systems of the Therapeutic Laser and System, Laser Beam Delivery, Laser Control System, Position and Shape Determination, Patient Interface, and Bean Directing Devices and Subsystems General teachings disclosed in this specification, and combinations and variations of each of these; as well as, one or more of the embodiments, processes, methods, features, functions, parameters, components, or systems provided in one or more of the other Examples.

Example 1

Figure 3:
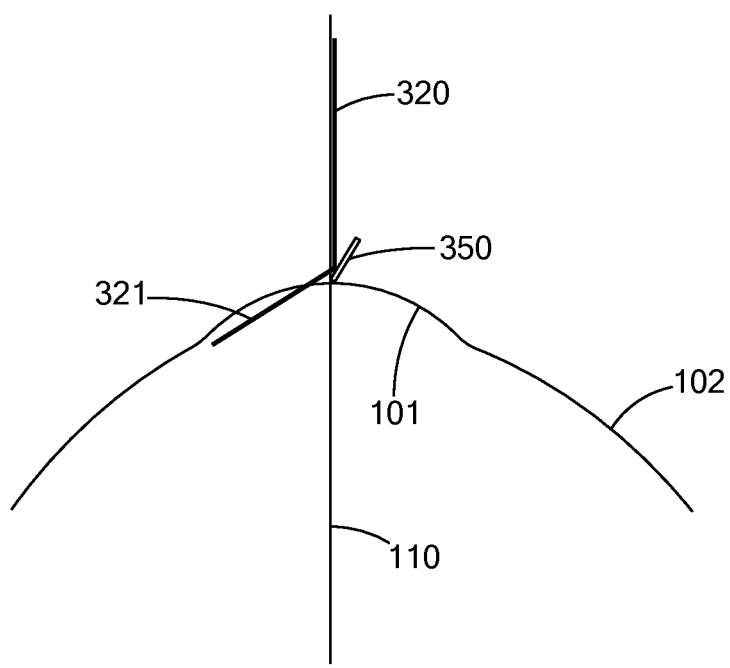
FIG. 3 is a cross sectional schematic view of an embodiment of a system for directing laser beams in accordance with the present inventions.

An embodiment of a laser beam path and beam directing device is shown in FIG. 3.

Example 2

Figure 4:
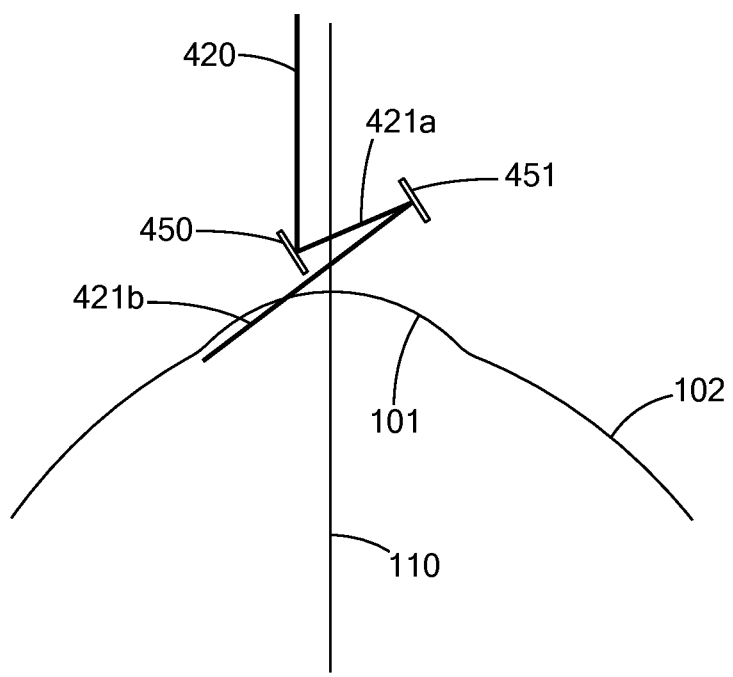
FIG. 4 is a cross sectional schematic view of an embodiment of a system for directing laser beams in accordance with the present inventions.

An embodiment of a laser beam path and beam directing device is shown in FIG. 4.

Example 3

Figure 5:
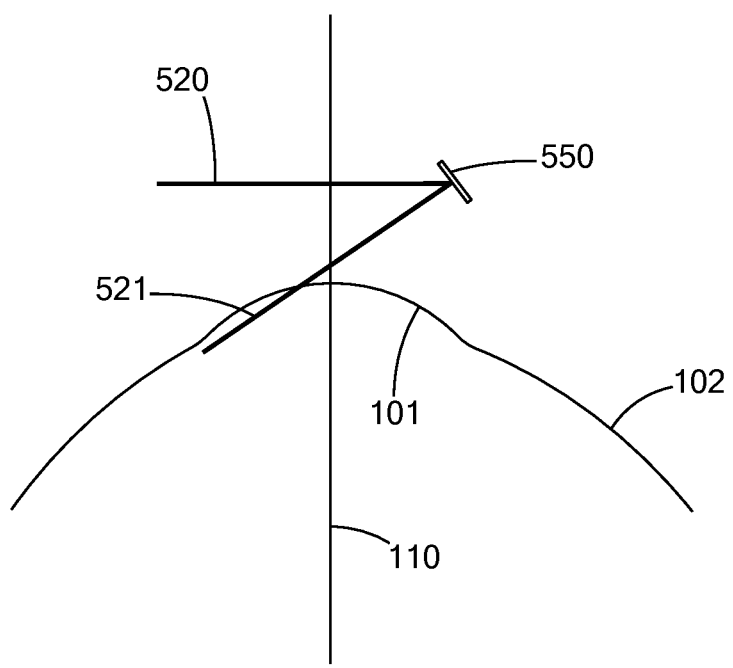
FIG. 5 is a cross sectional schematic view of an embodiment of a system for directing laser beams in accordance with the present inventions.

An embodiment of a laser beam path and beam directing device is shown in FIG. 5.

Example 4

Figure 6:
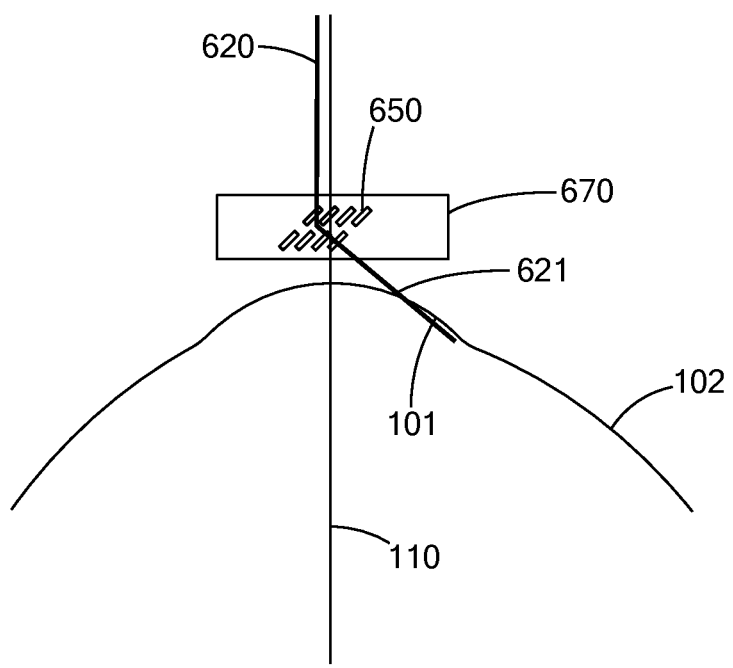
FIG. 6 is a cross sectional schematic view of an embodiment of a system for directing laser beams in accordance with the present inventions.

An embodiment of a laser beam path and beam directing device is shown in FIG. 6.

Example 5

The beam paths and optical systems of embodiments of the configurations of Examples 1 to 4 are configured to and used for imaging and diagnostic purposes. These beam paths and optical systems provide for the ability to get detailed images of the drain angle, trabecular mesh and the area of the eye where the iris and cornea meet. This imaging is of the entire 360° of these internal structures and area of the eye. The angle of viewing of these internal structures provides the ability to obtain images that can be better processed with imaging processing software and analyzed with imaging analysis software, then prior systems and techniques.

In this manner the images from the systems of the present inventions can be enhanced, so as to provide greater detail of these internal structures. These enhanced images provide several benefits. They provide the ability for greater clinical studies of conditions of the eye. They provide the ability to develop and use better MIGS. The provide the ability to have or match MIGS, even custom MIGS, to particular physical manifestation in the eye.

The laser system can have a data base, that is local or shared on the cloud as part of a network, that is used by a computer system that evaluates images and makes predictive recommendations for specific types of MIGS for the conditions observed from analysis of the images. Artificial intelligence systems and technology can be used to increase the accuracy and predictive benefits obtainable from these enhanced images and these predictive processes.

Example 6

Figure 7A:
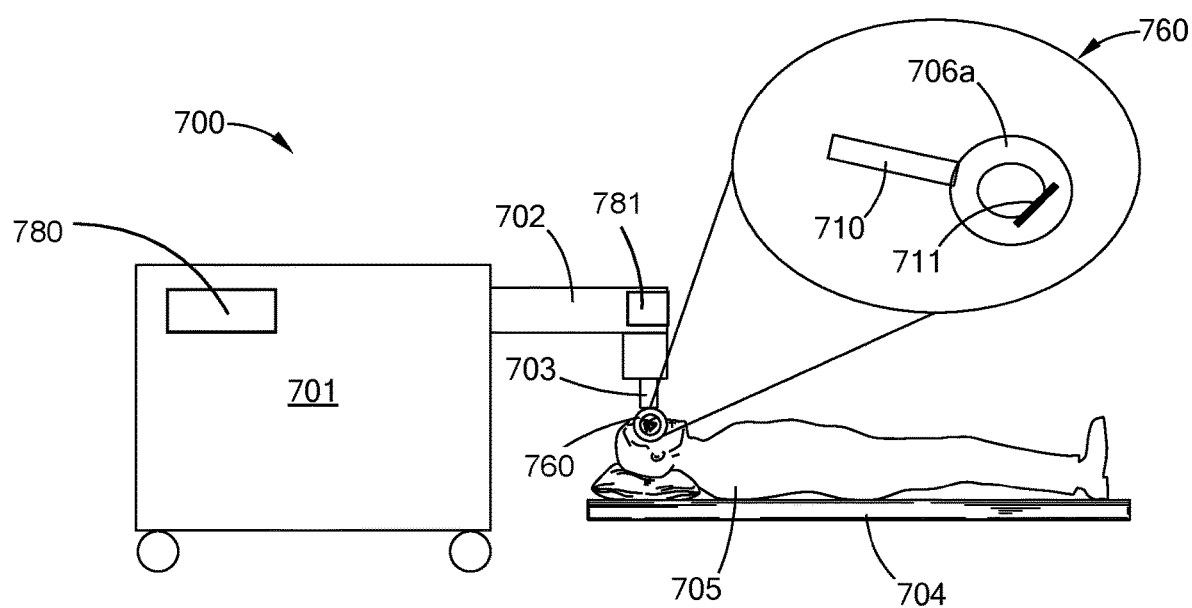
FIG. 7A is a schematic view of an embodiment of a laser system in accordance with the present inventions.

Turning to FIG. 7A laser surgery system 700 has a laser system 701 for providing a therapeutic laser beam. The laser system 701 contains the other devices and systems discussed in this specification and known to those of skill in the art for providing a therapeutic laser beam in a predetermined laser beam pattern to a structure of the eye. The laser system 701 has laser delivery conduit 702, which could be an arm, an arm and laser deliver head, a laser delivery head, or similar devices for housing a laser beam path, and the optical components to define that path, which the laser beam travels on, and for directing the laser beam through a PID 703 to an eye of a patient 705. It being understood that imaging beam paths, and images, are also transmitted through PID 703 and conduit 702 to laser system 701.

The system has a control system 780 and a device for determining the shape and position of a structure of the eye 781. The determining device 781 can also be used to detect and determine the position of the near eye directing system, the beam directing device and both, with respect to the laser and laser beam paths. The control system 780 is in control communication with the determining device 781. The control system 780 has a predetermined laser shot pattern. The predetermined laser beam shot pattern can be a predetermined laser beam shot pattern configured for the delivery of a laser beam to an area of the eye where an iris and a cornea meet, which preferably is a predetermined MIGS procedure laser beam shot pattern. In the manner the system is configured to deliver and delivers the predetermined laser beam pattern precisely to the beam directing device and precisely to the area of the eye where the iris and cornea meet, including to the drain angle and the trabecular mesh.

The system 700 has a near eye beam directing system 760. The near eye directing system 760 has a suction ring 706*a*, configured for attaching to and fixing on the outer surface of the eye. The near eye directing system 760 has a positioning device 710, e.g., a handle. The near eye directing system 760 has a beam directing device 711. In embodiments the beam directing device 711 can be one of the beam directing devices disclosed and discussed in the Beam Directing Devices and Sub-Systems-Generally section of this Specification.

In this manner the near eye beam directing system 760, the beam directing device 711 (i.e., the beam director), the control system 780 and the device for the determining the shape and position of the structure of the eye 781 are configured to provide the therapeutic laser beam in the predetermined laser shot pattern along the laser beam path to an area of the eye where an iris and a cornea meet.

In this embodiment the near eye beam directing system 760 is not connected or physically attached to the laser system 701, the conduit 702 or the PID 703. The PID 703 does not contact and is not attached to the eye.

Example 6A

The near eye beam directing system 760 has the device and beam path of Example 1.

Example 6B

The near eye beam directing system 760 has the device and beam path of Example 2.

Example 6C

The near eye beam directing system 760 has the device and beam path of Example 3.

Example 6D

The near eye beam directing system 760 has the device and beam path of Example 4.

Example 7

Figure 7B:
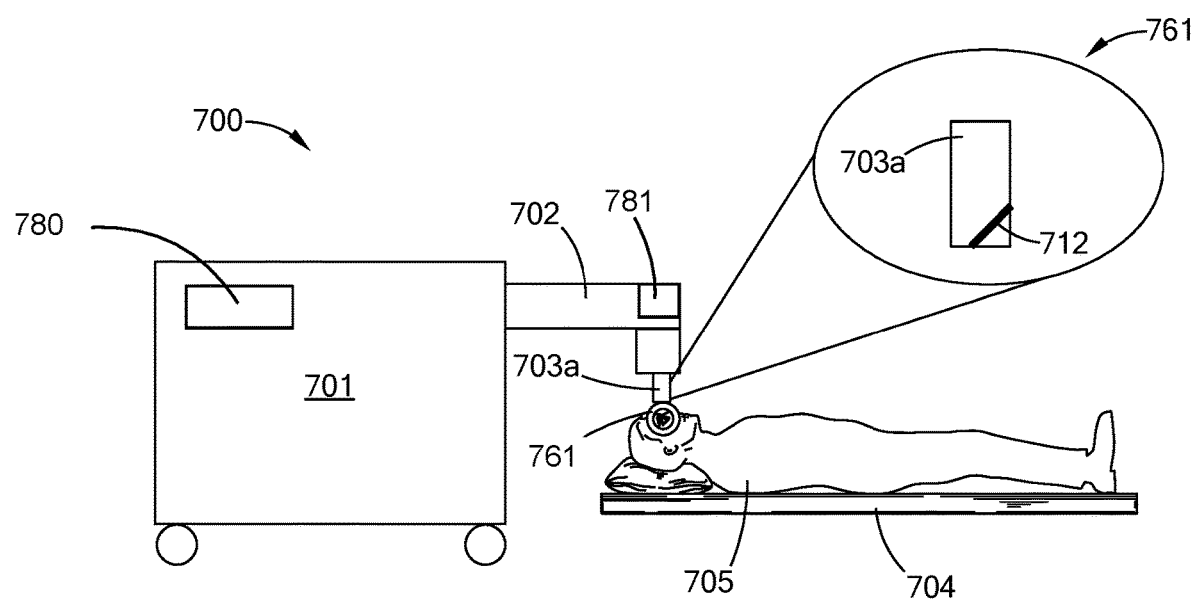
FIG. 7B is a schematic view of an embodiment of a laser system in accordance with the present inventions.
Figure 8:
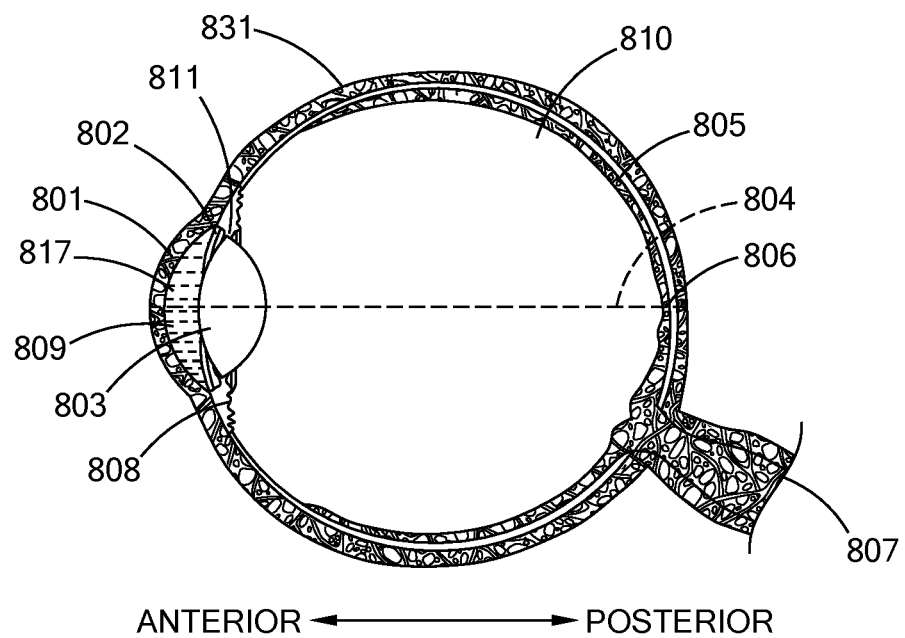
FIG. 8 is a cross section of the human eye.
Figure 8A:
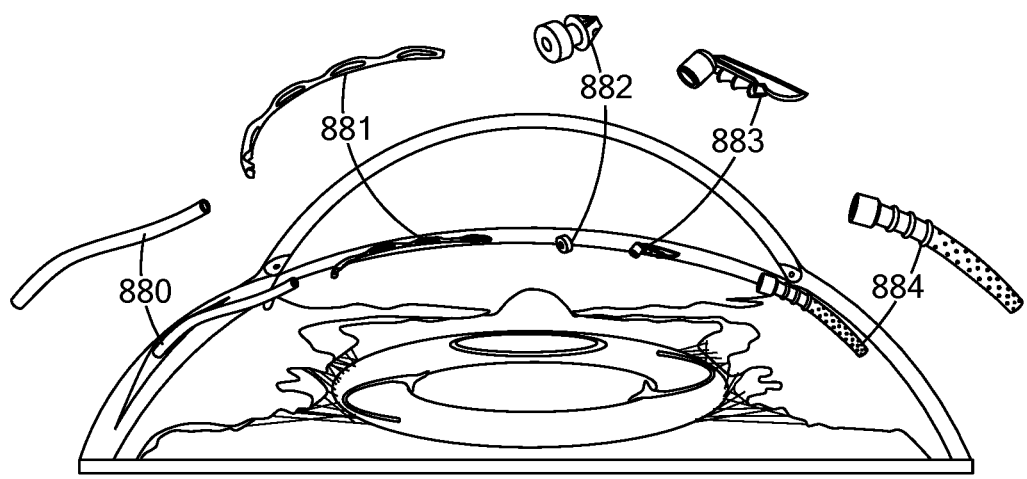
FIG. 8A is a perspective cross sectional view of multiple MIGS devices that can be utilized using embodiments of the present laser therapies, devices and systems in accordance with the present inventions.
Figure 8B:
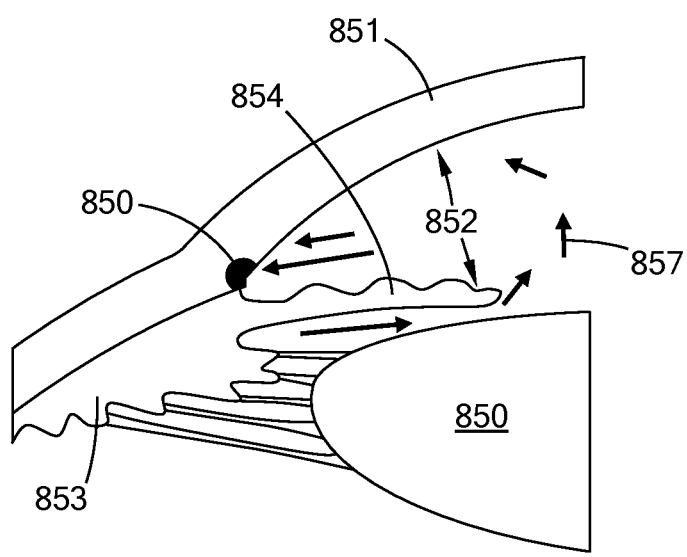
FIG. 8B is a cross sectional schematic view of the eye showing an open drainage angle.
Figure 8C:
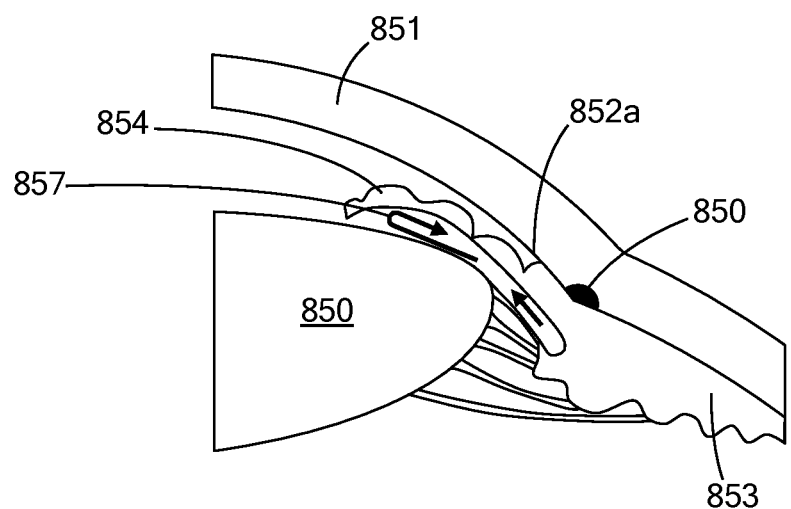
FIG. 8C is a cross sectional schematic view of the eye showing a closed drainage angle.

Turning to FIG. 7B the embodiment has the same laser system 700 of Example 6. However, in the embodiment of this Example 7 the laser surgery system 700 has a PID 703*a* that is configure to engage with and mechanically connect to the near eye beam directing system 761.

In this embodiment the PID 703a also is, and is configured to function as, the near eye beam directing system 761. Thus, in this embodiment the near eye directing system 761 physically engages, e.g., is attached to, both the eye and the laser system 701. The near eye directing system 761 has a beam directing device 712. In embodiments the beam directing device 712 can be one of the beam directing devices disclosed and discussed in the Beam Directing Devices and Sub-Systems-Generally section of this Specification.

In this embodiment the near eye beam directing system 760, which is a part of the PID 703a, is connected and physically attached to the laser system 701 through the conduit 702.

In this manner the near eye beam directing system 760, the beam directing device 712 (i.e., the beam director), the control system 780 and the device for the determining the shape and position of the structure of the eye 781 are configured to provide the therapeutic laser beam in the predetermined laser shot pattern along the laser beam path to an area of the eye where an iris and a cornea meet.

Example 7A

The near eye beam directing system 761 has the device and beam path of Example 1.

Example 7B

The near eye beam directing system 761 has the device and beam path of Example 2.

Example 7C

The near eye beam directing system 761 has the device and beam path of Example 3.

Example 7D

The near eye beam directing system 761 has the device and beam path of Example 4.

HEADINGS AND EMBODIMENTS

It should be understood that the use of headings in this specification is for the purpose of clarity, reference, and is not limiting in any way. Thus, the processes compositions, and disclosures described under a heading should be read in context with the entirely of this specification, including the various examples. The use of headings in this specification should not limit the scope of protection afford the present inventions.

It is noted that there is no requirement to provide or address the theory underlying the novel and groundbreaking processes, laser operations, and laser patterns, enhanced and improved vision, or other beneficial features and properties that are the subject of, or associated with, embodiments of the present inventions. Nevertheless, various theories are provided in this specification to further advance the art in this area. The theories put forth in this specification, and unless expressly stated otherwise, in no way limit, restrict or narrow the scope of protection to be afforded the claimed inventions. These theories many not be required or practiced to utilize the present inventions. It is further understood that the present inventions may lead to new, and heretofore unknown theories to explain the function-features of embodiments of the methods, laser patterns, laser operations, functions of the eye, devices and system of the present inventions; and such later developed theories shall not limit the scope of protection afforded the present inventions.

The various embodiments of devices, systems, laser shot patterns, activities, and operations set forth in this specification may be used with, in or by, various measuring, diagnostic, surgical and therapeutic laser systems, in addition to those embodiments of the Figures and disclosed in this specification. The various embodiments of devices, systems, laser shot patterns, activities, and operations set forth in this specification may be used with: other measuring, diagnostic, surgical and therapeutic systems that may be developed in the future: with existing measuring, diagnostic, surgical and therapeutic laser systems, which may be modified, in-part, based on the teachings of this specification; and with other types of measuring, diagnostic, surgical and therapeutic systems. Further, the various embodiments of devices, systems, laser shot patterns, activities, and operations set forth in this specification may be used with each other in different and various combinations. Thus, for example, the configurations provided in the various embodiments of this specification may be used with each other. For example, the components of an embodiment having A, A' and B and the components of an embodiment having A", C and D can be used with each other in various combination, e.g., A, C, D, and A. A" C and D, etc., in accordance with the teaching of this Specification. Thus, the scope of protection afforded the present inventions should not be limited to a particular embodiment, configuration or arrangement that is set forth in a particular embodiment, example, or in an embodiment in a particular Figure.

The inventions may be embodied in other forms than those specifically disclosed herein without departing from their spirit or essential characteristics. The described embodiments are to be considered in all respects only as illustrative and not restrictive.

What is claimed:
1. A system comprising:
a therapeutic laser for providing a therapeutic laser beam;
a laser delivery conduit coupled to the therapeutic laser;
a determining device for determining a shape and position of a structure of an eye;
a patient interface device (PID) configured to couple to and decouple from the laser delivery conduit and to maintain a constant distance between the determining device and the structure of an eye without attaching to the eye;
a control system comprising a predetermined minimally-invasive glaucoma surgeries (MIGS) procedure laser shot pattern; wherein (i) the determining device for determining the shape and position of the structure of the eye and (ii) the therapeutic laser for providing the therapeutic laser beam are in control communication with the control system; and
a near eye beam directing device comprising a beam director, wherein the near eye beam directing device is physically detached from the PID and the laser delivery conduit, and is configured to:
attach to a surface of the eye to optically couple the beam director with the therapeutic laser to receive the therapeutic laser beam,
maintain the beam director less than 5 mm above the surface of the eye, and direct the therapeutic laser beam along a directed laser beam path having a beam path angle of greater than 25° relative to an optical axis of the eye; and wherein, the near eye beam directing device, the control system and the determining device are configured to provide the therapeutic laser beam in the predetermined MIGS procedure laser shot pattern along the directed laser beam path to an area of the eye where an iris and a cornea meet while the PID is the constant distance from the eye and the near eye beam directing device is physically detached from the PID and attached to the eye.

2. The system of claim 1, wherein the determining device comprises an OCT device.

3. The system of claim 1, wherein the area of the eye where the iris and the cornea meet comprises one of a drain angle and a trabecular mesh.

4. The system of claim 1, wherein the beam director comprises a plurality of digital micromirrors (DM).

5. The system of claim 1, wherein the determining device is configured to provide images of the area of the eye where the iris and the cornea meet along the directed laser beam path.

6. The system of claim 1, wherein the determining device is configured to determine one or more of the shape and the position of the area where the iris and the cornea meet along the directed laser beam path.

7. The system of claim 1, wherein:
the near eye beam directing device comprises a suction ring,
the beam director is part of the suction ring, and
the suction ring is configured to couple to the surface of the eye.

8. The system of claim 7, wherein the near eye beam directing device comprises a handle coupled to the suction ring.

9. The system of claim 1, wherein the determining device is positioned on the laser delivery conduit.

10. The system of claim 1, wherein:
the determining device comprises a Scheimpflug device positioned relative to the near eye beam directing device and configured to output a light beam into the near beam directing device, and
the near beam directing device is configured to direct the light beam along a light path coincident with the directed laser beam path and to direct an image beam along an image path coincident with the directed laser beam path back to the Scheimpflug device.

11. The system of claim 1, further comprising a light illuminating and receiving subsystem positioned relative to the near eye beam directing device and configured to output a light beam into the near beam directing device, wherein the near beam directing device is configured to direct the light beam along a light path coincident with the directed laser beam path and to direct an image beam along an image path coincident with the directed laser beam path back to the light illuminating and receiving subsystem.

* * * * *